US00PP12473P2

(12) United States Plant Patent
Utecht

(10) Patent No.: US PP12,473 P2
(45) Date of Patent: Mar. 19, 2002

(54) GERANIUM PLANT NAMED 'FISORCHI'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/772,937

(22) Filed: Jan. 31, 2001

(51) Int. Cl.[7] ..... A01H 5/00
(52) U.S. Cl. ..... Plt./328
(58) Field of Search ..... Plt./327, 328, 325

(56) References Cited

PUBLICATIONS

GTITM UPOVROM Citation for 'Fisorchi' as per QZ PBR 991469; Oct. 20, 1999.*
Fischer–Schmülling Plant Alliance Catalog featuring 'Fisorchi' on p. 17 (2001).
Official Gazette of the Community Plant Variety Office Dec. 15, 1999; European Union Application, denomination, decision for 'Fisorchi'.
German Application for 'Fisorchi' Dec. 15, 1998.
German Proprosed Denomination for 'Fisorchi' Aug. 15, 1999.
Plant Varieties Journal, Jan. 2001, No. 38, pp. 54–55 (Canada).

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisorchi', as described and illustrated, and particularly characterized by the combined features of very light pink and white, semi-double flowers, medium-sized inflorescences well above the foliage, early and rich flowering, uniform dark-green foliage, and relatively compact plant habit.

1 Drawing Sheet

BACKGROUND OF THE INVENTION

The present invention comprises a new and distinct cultivar of geranium, botanically known as *Pelargonium zonale*, and hereinafter referred to by the cultivar name 'Fisorchi'.

'Fisorchi' is a product of a planned breeding program which had the objective of creating new geranium varieties with very light pink flower color in combination with dark-green foliage. 'Fisorchi' originated from a hybridization made by the inventor Angelika Utecht in a controlled breeding program in Galdar, Gran Canaria, Spain, in 1996.

The female parent was the variety 'Roseball' (unpatented), Plant Breeder's Right 'Penbab' in Europe characterized by light-pink, semi-double flowers with distinct white eyes at the bases of upper petals, and medium green foliage with weak zonation. The male parent of 'Fisorchi' was a hybrid seedling, no. 1927-9 (unpatented), which is characterized by single-type white-pink eyes, dark-green foliage, and compact plant habit with poor branching characteristics.

'Fisorchi' was selected as one flowering plant within the progeny of the stated cross by Angelika Utecht in 1997 in a controlled environment in Galdar, Gran Canaria, Spain. The first act of asexual reproduction of 'Fisorchi' was accomplished when vegetative cuttings were taken from the initial selection in the fall of 1993 in a controlled environment in Galdar, Gran Canaria, Spain, by, or under the supervision of, Angelika Utecht.

Horticultural examination of plants grown from cuttings of the plant initiated in May 1998 in Hillscheid, Federal Republic of Germany, and continuing thereafter, has demonstrated that the combination of characteristics as herein disclosed for 'Fisorchi' are firmly fixed and are retained through successive generations of asexual reproduction.

'Fisorchi' has not been observed under all possible environmental conditions. The phenotype may vary significantly with variations in environment such as temperature, light intensity and day length.

BRIEF DESCRIPTION OF THE INVENTION

The following observations, measurements, and comparisons describe plants grown in Hillscheid, Germany, and in Langley, British Columbia, Canada, under greenhouse conditions which approximate those generally used in commercial practice.

The following traits have been repeatedly observed and are determined to be basic characteristics of 'Fisorchi' in combination distinguish this geranium as a new and distinct cultivar:

1. Very light pink flowers with large white center;

2. Round, medium-sized inflorescences, well above the foliage;

3. Uniform, dark-green foliage without or with only very weak zonation;

4. Weak to medium vigor, relatively compact plant habit; and

5. Early spring flowering response, floriferous throughout the summer.

Of the many commercial cultivars known to the present inventor, the most similar in comparison to 'Fisorchi' is the variety 'Balsholila' (U.S. Plant Pat. No. 11,679), and the parental variety 'Roseball'. In comparison to 'Balsholila', 'Fisorchi' has a lighter flower color, more round shaped flowers, in contrast to the slightly zygomophic flowers of 'Fisorchi', and more compact plant habit. In comparison to 'Roseball', 'Fisorchi' has a lighter flower color and distinctly darker green foliage.

BRIEF DESCRIPTION OF THE DRAWING

The accompanying photographic drawing shows typical flower and foliage characteristics of 'Fisorchi' with colors being as true as possible with an illustration of this type. The measurements were taken in Langley, British Columbia, Canada, on Jul. 20, 2000, 15 weeks after planting of rooted cuttings into 6 inch pots. The plants had not been pinched.

In the following description color references are made to The Royal Horticultural Society Colour Chart (R.H.S.). The color values were determined indoors from plants developed in a green-house in May 2000, in Hillscheid, Germany.

Classification:

*Botanical*.—A hybrid of the species *Pelargonium zonale* L'Hérit.

*Commercial*.—Zonal geranium, cv. 'Fisorchi'.

Inflorescence:

*Umbel*.—Shape: Almost semi-spherical. Average diameter: 116 mm. Average depth: 55 mm. Peduncle length: 162 mm. Peduncle color: Green, RHS 137 C, slight infusion of anthocyanin in parts, brownish, RHS 179 A. Pedicel length: 31 mm. Pedicel color: About RHS 179 B, with light green at the lower end, RHS 144 A. Number of flowers per umbel: About 30. Lastingness of the umbel: Approximately 17–18 days at 18° C.

*Corolla*.—Average diameter: 49 mm. Form: Semi-double. Shape: Relatively large, round, weakly cup-shaped. Number of petals: 6–8. Size of petals: Upper petals are 27–28 mm long, 18–21 mm wide; lower petals are 23–24 mm long, 23–25 mm wide. Shape of petals: Obovate, attenuate base, upper end rounded, margin entire. Number of petaloids: 1–2. Color of petaloids: Upper surface is RHS 65 B, lower surface is RHS 65 D. Color (general tonality from a distance of three meters): Very light pink. Color of upper petals: From RHS 68 D to RHS 65 B. Markings of upper petals: Large white macules at the bases, RHS 155D. Color of lower petals:: From RHS 68 D to RHS 65 B, and small white RHS 155 D to very light pink RHS 69 B bases. Color of lower surface of petals: Light pink RHS 65 B near the margin, to lighter shades of pink from RHS 65 C to RHS 65 D, with white 155 D in the middle. Color of sepals: Outer suface green, RHS 143 C, reddish-brown RHS 179 B at the base, inner surface light green RHS 143 C, base RHS 179 A. Size of sepals: 11–12 mm in length, 4 mm in diameter for the largest, upper sepal, 2–3 mm in diameter for the other sepals. Shape of sepals: Linear to lanceolate, acute tip, base truncate, margin entire, surface with weak, short pubescence. Number of sepals: 5.

*Bud: (just prior to petals unfolding)*.—Shape: Elliptical. Color (lower part — sepals): Mainly green, RHS 137 D, weak reddish-brown spot, RHS 179 B, at the base. Color (upper part — petals): Cream-pink, RHS 49 B. Length: 16 mm. Width: 8 mm.

*Reproductive organs*.—Androecium: 7–9 fertile anthers, whitish to light pink filaments, orange pollen, RHS 33 A, plentiful quantity of pollen produced. Gynoecium: 5–6-lobed, light pink stigma, pink filament, one pistil per flower. Fertility/Seed set: Occasionally a few seeds are developed, oblong, 4–5 mm in length, brown, RHS 177 B.

*Spring flowering response period*.—In Hillscheid, Germany, in 2000, plants had on average 1.7 flowers opened 9 weeks after planting of rooted cuttings.

*Outdoor flower production*.—Rich flowering, the flower count in 2000, in Hillscheid, Germany, indicated about 5 inflorescences per plant in mid May.

*Durability*.—Good stability of flower color, relatively good rain resistance.

*Lastingness of the individual bloom*.—Approximately 8 days at 18° C.

*Fragrance*.—None.

Plant:

*Foliage*.—Shape: Kidney-shaped. Base: Cordate with open gap between lower ends of the leaf. Margin: Bicrenated, somewhat wavy. Texture: Upper surface is slightly velvety. Size of leaf: 77 mm wide, approximately 50 mm long. Color of upper surface: Dark-green, approximately RHS 137 A. Color of undersurface: RHS 137 C. Color of zonation: Absent or very weak, darker green, RHS 147 A. Size of petioles: 50–60 mm long, 3 mm wide. Color of petioles: RHS 143 A.

*General appearance and form*.—Stem color: Light green, RHS 137 D. Branching pattern: 2.9 branches. Plant size: 21 cm as measured from the soil to the surface of the foliage canopy, without inflorescences; 27.9 cm wide.

*Disease pest resistance susceptibility*.—None observed to date.

I claim:

1. A new and distinct cultivar of geranium plant named 'Fisorchi', as described and illustrated.

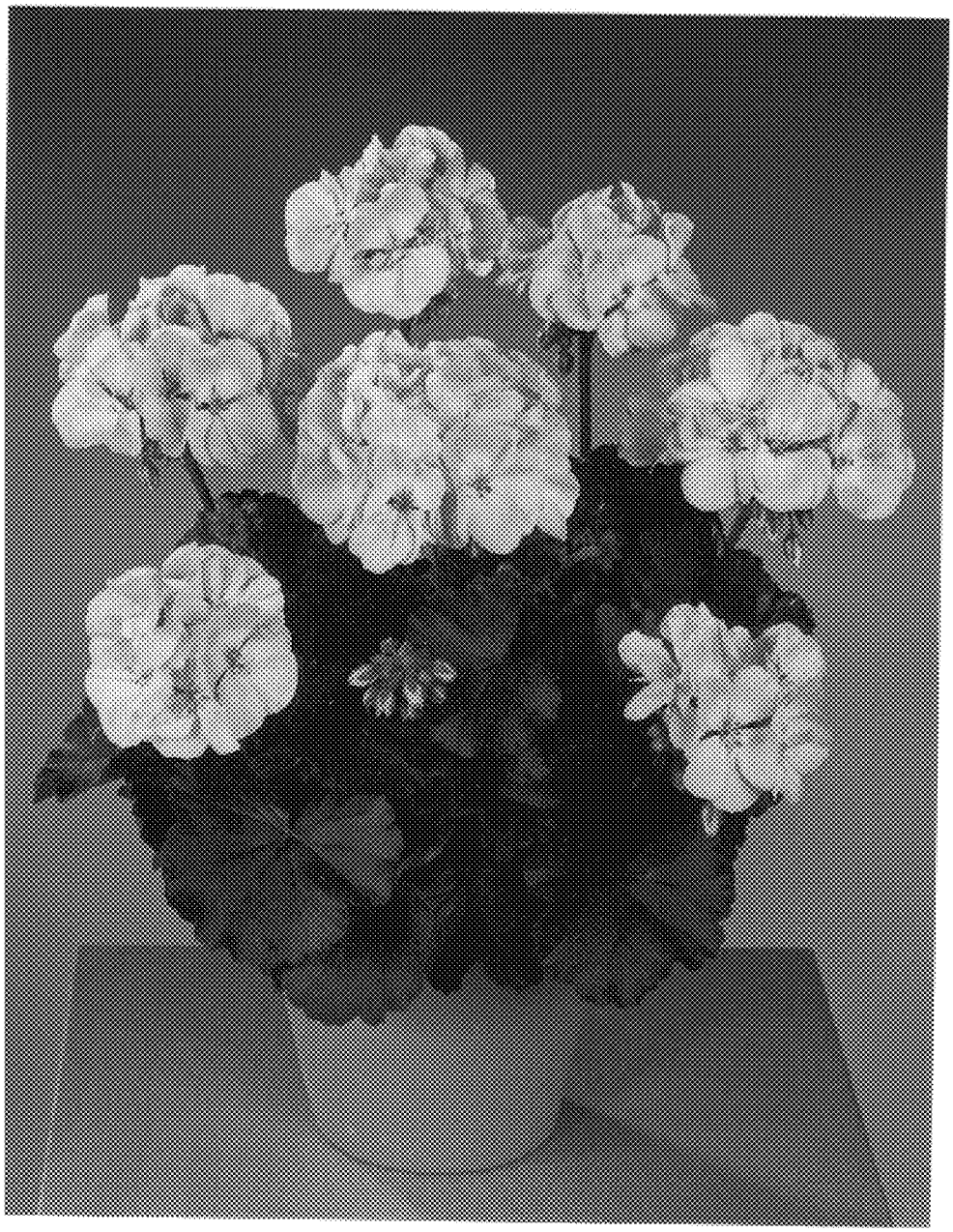

* * * * *